(12) United States Patent
Yeoh et al.

(10) Patent No.: US 6,200,554 B1
(45) Date of Patent: *Mar. 13, 2001

(54) CONDITIONING SHAMPOO COMPOSITIONS HAVING IMPROVED SILICONE DEPOSITION

(75) Inventors: Thean Yeow Yeoh, Mason; Timothy Woodrow Coffindaffer, Loveland, both of OH (US); Hirotaka Uchiyama, Kobe (JP); John Gregory Schroeder, Kobe (JP); Yoshinari Okuyama, Kobe (JP)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/733,046

(22) Filed: Oct. 16, 1996

(51) Int. Cl.$^7$ ........................................ A61K 7/06
(52) U.S. Cl. ........................ 424/70.12; 424/70.11; 424/70.31; 514/778; 514/780; 514/782
(58) Field of Search .................. 424/70.12, 70.11, 424/70.31; 514/778, 780, 782

(56) References Cited

U.S. PATENT DOCUMENTS

| | | | |
|---|---|---|---|
| 2,897,178 | 7/1959 | Hill | 260/45.9 |
| 2,921,047 | 1/1960 | Smith | 260/45.9 |
| 2,934,518 | 4/1960 | Smith | 260/45.85 |
| 2,942,978 | 6/1960 | Segel et al. | 99/48 |
| 2,942,979 | 6/1960 | Segel et al. | 99/48 |
| 2,942,980 | 6/1960 | Segel et al. | 99/48 |
| 2,991,229 | 7/1961 | Ivison | 424/49 |
| 2,999,068 | 9/1961 | Pilcher et al. | 252/137 |
| 3,201,257 | 8/1965 | Hamon et al. | 99/113 |
| 3,201,367 | 8/1965 | Smith | 260/45.9 |
| 3,242,115 | 3/1966 | McGary | 260/29.2 |
| 3,326,849 | 6/1967 | Kelly et al. | 260/45.8 |
| 3,374,275 | 3/1968 | Dickey | 260/611.5 |
| 3,634,315 | 1/1972 | Hattori et al. | 260/45.8 |
| 3,645,950 | 2/1972 | Stratta | 260/29.2 |
| 3,729,441 | 4/1973 | Tomomatsu | 260/45.95 |
| 3,783,872 | 1/1974 | King | 128/290 |
| 3,811,349 | 5/1974 | Jennings | 83/14 |
| 3,944,663 | 3/1976 | Weiss et al. | 424/78 |
| 4,058,474 | 11/1977 | Keyes et al. | 252/160 |
| 4,108,800 | 8/1978 | Froehlich | 252/541 |
| 4,148,743 | 4/1979 | Schubert | 252/132 |
| 4,169,067 | 9/1979 | Joshi | 252/132 |
| 4,192,862 | 3/1980 | Pengilly | 424/47 |
| 4,211,681 | 7/1980 | Braun et al. | 260/29.2 R |
| 4,329,334 | 5/1982 | Su et al. | 424/70 |
| 5,114,706 | * 5/1992 | Duvel | 424/70 |
| 5,152,914 | * 10/1992 | Forster et al. | 252/174 |
| 5,169,622 | * 12/1992 | Kopolow et al. | 424/47 |
| 5,275,755 | 1/1994 | Sebag et al. | 252/174.15 |
| 5,306,434 | * 4/1994 | Schueller et al. | 252/8.8 |
| 5,346,642 | * 9/1994 | Patel et al. | 353/174.21 |
| 5,354,564 | * 10/1994 | Borish et al. | 424/490 |
| 5,358,667 | 10/1994 | Bergmann | 252/547 |
| 5,362,484 | * 11/1994 | Wood et al. | 424/70.12 |
| 5,393,519 | * 2/1995 | Dowell et al. | 424/70.11 |
| 5,932,202 | * 8/1999 | Guskey et al. | 424/70.19 |

FOREIGN PATENT DOCUMENTS

| | | | |
|---|---|---|---|
| 0 407 042 A2 | 1/1991 | (EP) | A61K/7/06 |
| 06321742 | 5/1993 | (JP) . | |
| 96/32092 | 10/1996 | (WO) | A61K/7/48 |

OTHER PUBLICATIONS

Union Carbide, Specialty Chemicals and Plastics Division, Danbury, CT, Booklet, "Patent Literature Review of POLYOX Resin Applications".

* cited by examiner

Primary Examiner—Thurman K. Page
Assistant Examiner—Lakshmi Channavajjala
(74) Attorney, Agent, or Firm—Lucy Elandjian; Joan B. Tucker; William J. Winter

(57) ABSTRACT

Disclosed are conditioning shampoo compositions which provide improved hair or skin conditioning performance. These compositions comprise a detersive surfactant, select ethoxylated fatty alcohols having a fatty alcohol moiety containing from about 6 to about 30 carbon atoms and an ethoxylate chain containing from about 5 to about 150 moles of ethoxylation, a nonvolatile conditioning agent, preferably a nonvolatile silicone conditioning agent, having an average particle size of from about 5 um to about 2000 um, and water. The select ethoxylated fatty alcohols provide improved hair or skin conditioning by improving silicone deposition of large particle conditioning agents onto the hair or skin.

24 Claims, No Drawings

CONDITIONING SHAMPOO COMPOSITIONS HAVING IMPROVED SILICONE DEPOSITION

FIELD OF THE INVENTION

The present invention relates to conditioning shampoo compositions which provide improved hair conditioning performance. These compositions comprise a detersive surfactant, select ethoxylated fatty alcohols, and a hair conditioning agent having a selectively large particle size.

BACKGROUND OF THE INVENTION

Conditioning shampoos comprising various combinations of detersive surfactant and hair conditioning agents are known. These shampoo products typically comprise an anionic detersive surfactant in combination with a conditioning agent such as silicone, hydrocarbon oil, fatty esters, or combinations thereof. These shampoos have become more popular among consumers as a means of conveniently obtaining hair conditioning and hair cleansing performance all from a single hair care product.

Many conditioning shampoos, however, do not provide sufficient deposition of conditioning agents onto hair during the shampooing process. Without such deposition, large proportions of conditioning agent are rinsed away during the shampooing process and therefore provide little or no conditioning benefit. Without sufficient deposition of the conditioning agent on the hair, relatively high levels of conditioning agents may be needed in the shampoo composition to provide adequate hair conditioning performance. Such high levels of a conditioning agent can substantially increase raw material cost.

Obtaining good deposition of a conditioning agent onto hair is further complicated by the action of detersive surfactants in the shampoo. Detersive surfactants are designed to carry away or remove, oil, grease, dirt, and particulate matter from the hair and scalp. In doing so, the detersive surfactants can also interfere with deposition of the conditioning agent, and carry away both deposited and non deposited conditioning agent during rinsing. This further reduces deposition of the conditioning agent onto the hair after rinsing, thus further reducing hair conditioning performance.

One known method for improving deposition of a hair conditioning agent onto hair involves the use of certain cationic deposition polymers. These polymers provide improved deposition of the conditioning agent onto hair, and can also inherently provide improved wet hair conditioning independent of such improved deposition. These cationic polymers, however, introduce compatibility problems when formulating with anionic shampoo components, and can also cause wet hair to feel excessively smooth or over conditioned. Moreover, these cationic deposition polymers are most effective when used with smaller particle conditioning agents having an average particle size of less than 5 um, more typically less than about 2 um. Deposition of large particle silicone conditioning systems are not typically improved by the use of cationic polymers.

It has now been found that shampoo compositions containing select ethoxylated fatty alcohols can be used to improve the deposition of a conditioning agent onto hair or skin, without the reliance upon cationic deposition polymers, provided that the hair or skin conditioning agent is in the form of large dispersed particles having an average particle size of at least 5 um. These select ethoxylated fatty alcohols are especially effective at improving deposition of dispersed hair conditioning agents onto hair or skin when used in combination with an anionic detersive surfactant in a shampoo or other surfactant composition. These select fatty alcohol ethoxylates have from about 5 to about 150 moles of ethoxylation, and an attached fatty alcohol moiety having from about 6 to about 30 carbon atoms.

It is therefore an object of the present invention to provide a conditioning shampoo composition for use on hair or skin with improved conditioning performance, and further to provide such a composition with improved deposition of dispersed conditioning agents onto hair or skin without reliance upon cationic deposition polymers, and further to provide such a composition with improved deposition of dispersed conditioning agent particles having an average particle size of from about 5 microns up to about 2000 microns. It is yet another object of the present invention to provide a conditioning shampoo composition with improved conditioning performance using select ethoxylated fatty alcohols.

SUMMARY OF THE INVENTION

The present invention relates to a conditioning shampoo composition for use on hair or skin, which comprises:
  (a) from about 5% to about 50% by weight of a detersive surfactant selected from the group consisting of anionic surfactants, nonionic surfactants, amphoteric surfactants, zwitterionic surfactants, and mixtures thereof;
  (b) from about 0.1% to about 10% by weight of an ethoxylated fatty alcohol having a fatty alcohol moiety containing from about 6 to about 30 carbon atoms and an ethoxylate chain having from about 5 to about 150 moles of ethoxylation;
  (c) from about 0.01% to about 20% by weight of dispersed particles of a nonvolatile conditioning agent having an average particle size of from about 5 um to about 2000 um; and
  (d) from about 20% to about 94.85% by weight water.

The present invention also relates to methods of cleansing and conditioning hair or skin by using the composition herein. For hair care applications, the average particle size of the conditioning agent should range from about 5 um to about 500 um, and for skin care applications the average particle size of the conditioning agent preferably ranges from about 500 um to about 2000 um.

DETAILED DESCRIPTION OF THE INVENTION

The shampoo compositions of the present invention are aqueous systems comprising a detersive surfactant, select ethoxylated fatty alcohols, and hair conditioning agents having a selectively large particle size. Each of these components are described in detail hereinafter. The shampoo compositions of the present invention can comprise, consist of, or consist essentially of the essential elements and limitations of the invention described herein, as well as any of the additional or optional ingredients, components, or limitations described herein.

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials, unless otherwise specified.

Detersive Surfactant

The shampoo compositions of the present invention comprise a detersive surfactant suitable for use on hair or skin. Suitable surfactants include anionic surfactants, nonionic surfactants, amphoteric surfactants, zwitterionic surfactants, or mixtures thereof. The purpose of the detersive surfactant is to provide cleansing performance to the composition. The term detersive surfactant, as used herein, is intended to distinguish these surfactants from surfactants which are primarily emulsifying surfactants, i.e. surfactants which provide an emulsifying benefit and which have low cleansing performance. It is recognized that most surfactants have both detersive and emulsifying properties. It is not intended to exclude emulsifying surfactants from the present invention, provided the surfactant also possesses sufficient detersive properties to be useful herein.

Concentrations of the surfactant in the shampoo composition range from about 5% to about 50%, preferably from about 8% to about 30%, and more preferably from about 10% to about 25%, by weight of the composition.

Anionic Surfactants

Anionic surfactants useful herein include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to about 10, and M is hydrogen or a cation such as ammonium, alkanolammonium (e.g., triethanolammonium), a monovalent metal cation (e.g., sodium and potassium), or a polyvalent metal cation (e.g., magnesium and calcium). Preferably, M should be chosen such that the anionic surfactant component is water soluble. The anionic surfactant or surfactants should be chosen such that the Krafft temperature is about 15° C. or less, preferably about 10° C. or less, and more preferably about 0° or less. It is also preferred that the anionic surfactant be soluble in the composition hereof.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, Drew, *Surfactant Science and Technology* pp. 82–85, VCH Publishers, Inc. (New York, N.Y., USA), 1988 (ISBN 0-89573-399-0), which is incorporated by reference herein in its entirety.

In the alkyl and alkyl ether sulfates described above, preferably R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm oil, tallow, or the like, or the alcohols can be synthetic. Lauryl alcohol and straight chain alcohols derived from coconut oil and palm oil are preferred herein. Such alcohols are reacted with 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from 1 to about 4 moles of ethylene oxide. Such a mixture also comprises from 0% to about 20% by weight of $C_{12-13}$ compounds; from about 60% to about 100% by weight of $C_{14-15-16}$ compounds, from 0% to about 20% by weight of $C_{17-18-19}$ compounds; from about 3% to about 30% by weight of compounds having a degree of ethoxylation of 0; from about 45% to about 90% by weight of compounds having a degree of ethoxylation of from 1 to about 4; from about 10% to about 25% by weight of compounds having a degree of ethoxylation of from about 4 to about 8; and from about 0.1% to about 15% by weight of compounds having a degree of ethoxylation greater than about 8.

Other suitable anionic surfactants are the water-soluble salts of organic, sulfuric acid reaction products of the general formula $[R_1—SO_3—M]$ where $R_1$ is selected from the group consisting of a straight or branched chain, saturated aliphatic hydrocarbon radical having from about 8 to about 24, preferably about 10 to about 18, carbon atoms; and M is as previously described above in this section. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic surfactants are the reaction products of fatty acids esterified with isethionic acid and neutralized with sodium hydroxide where, for example, the fatty acids are derived from coconut or palm oil; or sodium or potassium salts of fatty acid amides of methyl tauride in which the fatty acids, for example, are derived from coconut oil. Other similar anionic surfactants are described in U.S. Pat. Nos. 2,486,921, 2,486,922, and 2,396,278, which are incorporated by reference herein in their entirety.

Other anionic surfactants suitable for use in the shampoo compositions are the succinates, examples of which include disodium N-octadecylsulfosuccinate; disodium lauryl sulfosuccinate; diammonium lauryl sulfosuccinate; tetra sodium N-(1,2-dicarboxyethyl)-N-octadecylsulfosuccinate; the diamyl ester of sodium sulfosuccinic acid; the dihexyl ester of sodium sulfosuccinic acid; and the dioctyl ester of sodium sulfosuccinic acid.

Other anionic surfactants suitable for use in the shampoo compositions are those that are derived from amino acids. Nonlimiting examples of such surfactants include N-acyl-L-glutamate, N-acyl-N-methyl-β-alanate, N-acylsarcosinate, and their salts.

Still other useful surfactants are those that are derived from taurine, which is also known as 2-aminoethanesulfonic acid. An example of such an acid is N-acyl-N-methyl taurate.

Other suitable anionic surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A specific alpha-olefin sulfonate mixture of the above type is described more fully in U.S. Pat. No. 3,332,880, to Pflaumer and Kessler, issued Jul. 25, 1967, which is incorporated by reference herein in its entirety.

Another class of anionic surfactants suitable for use in the shampoo compositions are the beta-alkyloxy alkane sulfonates. These compounds have the following formula:

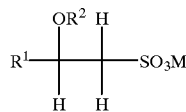

where $R^1$ is a straight chain alkyl group having from about 6 to about 20 carbon atoms, $R^2$ is a lower alkyl group having from about 1, preferred, to about 3 carbon atoms, and M is as hereinbefore described. Many other anionic surfactants suitable for use in the shampoo compositions are described in *McCutcheon's, Emulsifiers and Detergents*, 1989 Annual, published by M. C. Publishing Co., and in U.S. Pat. No. 3,929,678, which descriptions are incorporated herein by reference in their entirety. Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate, sodium N-lauroyl-L-glutamate, triethanol N-lauryoyl-L-glutamate, sodium N-lauroyl-N-methyl taurate, sodium N-lauroyl-N-methyl-o-aminopropionate, and mixtures thereof.

Amphoteric and Zwitterionic Surfactants

The shampoo compositions can comprise amphoteric and/or zwitterionic surfactants. Amphoteric surfactants suitable for use in the shampoo compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants suitable for use in the shampoo compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

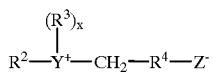

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom, and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocamidodimethylpropylsultaine, stearylamidododimethylpropylsultaine, laurylamidobis-(2-hydroxyethyl) propylsultaine, and the like. Preferred are amidohydroxysultaines such as the $C_{12}-C_{18}$ hydrocarbyl amidopropyl hydroxysultaines, especially $C_{12}-C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which is incorporated herein by reference in its entirety.

Other suitable amphoteric surfactants are the aminoalkanoates of the formula $R-NH(CH_2)_nCOOM$, the iminodialkanoates of the formula $R-N[(CH_2)_mCOOM]_2$ and mixtures thereof; wherein n and m are numbers from 1 to about 4, R is $C_8-C_{22}$ alkyl or alkenyl, and M is hydrogen, alkali metal, alkaline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric surfactants include those represented by the formula:

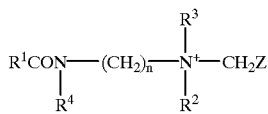

where $R^1$ is $C_8-C_{22}$ alkyl or alkenyl, preferably $C_{12}-C_{16}$, $R^2$ and $R^3$ is independently selected from the group consisting of hydrogen, $CH_2CO_2M$, $CH_2CH_2OH$, $CH_2CH_2OCH_2CH_2COOM$, or $(CH_2CH_2O)_mH$ wherein m is an integer from 1 to about 25, and $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate. Suitable materials of this type are marketed under the tradename MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are mono-carboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants, i.e. zwitterionic surfactants, suitable for use in the shampoo compositions are those represented by the formula:

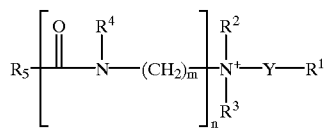

wherein:
R₁ is a member selected from the group consisting of

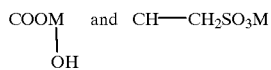

R₂ is lower alkyl or hydroxyalkyl;
R₃ is lower alkyl or hydroxyalkyl;
R₄ is a member selected from the group consisting of hydrogen and lower alkyl;
R₅ is higher alkyl or alkenyl;
Y is lower alkyl, preferably methyl;
m is an integer from 2 to 7, preferably from 2 to 3;
n is the integer 1 or 0;
M is hydrogen or a cation, as previously described, such as an alkali metal, alkaline earth metal, or ammonium. The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substitutents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethyl-carboxymethylbetaine, lauryl-bis-(2-hydroxyethyl) carboxymethylbetaine, stearyl-bis-(2-hydroxypropyl) carboxymethylbetaine, oleyldimethyl-gamma-carboxypropylbetaine, lauryl-bix-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the shampoo compositions include the amidocarboxybetaines, such as cocamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocamido-bis-(2-hydroxyethyl)-carboxymethylbetaine, etc. The amido sulfobetaines may be represented by cocamidodimethylsulfopropylbetaine, stearylamidodimethylsulfopropylbetaine, laurylamido-bis-(2-hydroxyethyl)-sulfopropylbetaine, and the like.

Nonionic Surfactants

The shampoo compositions of the present invention can comprise a nonionic surfactant, suitable examples of which include those compounds produced by condensation of alkylene oxide groups, hydrophilic in nature, with an organic hydrophobic compound, which may be aliphatic or alkyl aromatic in nature.

Preferred nonlimiting examples of nonionic surfactants for use in the shampoo compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(4) long chain tertiary phosphine oxides of the formula $[RR'R''P \rightarrow O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R'' are each alkyl or monohydroxy-alkyl groups containing from about 1 to about 3 carbon atoms;

(5) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties; and (6) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside which is commercially available from Henkel, ICI Americas, and Seppic.

Ethoxylated Fatty Alcohol

The shampoo compositions of the present invention comprise from about 0.1% to about 10%, preferably from about 0.5% to about 5%, and more preferably from about 1% to about 3% of select ethoxylated fatty alcohols. The select ethoxylated fatty alcohols provide improved deposition of hair or skin conditioning agents (described hereinafter), provided that such agents are dispersed particles having an average particle size of from about 5 um to about 2000 um, preferably from about 5 um to about 500 um for use in hair care products, and preferably from about 500 um to about 2000 um for use in skin care products.

The select ethoxylated fatty alcohols for use in the shampoo composition of the present invention are compounds having an ethylene oxide moiety corresponding to the formula $(OCH_2CH_2)_n$, wherein n is from about 5 to about 150, preferably from about 6 to about 31, and more preferably from about 7 to about 21 moles of ethoxylation. Moreover, the ethoxylated fatty alcohols useful herein are those having a fatty alcohol moiety having from about 6 to about 30 carbon atoms, preferably from about 8 to about 22 carbon atoms, and more preferably from about 10 to about 19 carbon atoms. These fatty alcohols can be straight or branched chain alcohols and can be saturated or unsaturated.

Nonlimiting examples of suitable ethoxylated fatty alcohols for use in the shampoo composition include ethoxylated fatty alcohols derived from coconut fatty alcohols, the ceteth series of compounds such as ceteth-5 through ceteth-45, which are ethylene glycol ethers of cetyl alcohol, wherein the numeric designation indicates the number of ethylene oxide moieties present; the steareth series of compounds such as steareth-5 through steareth-100, which are ethylene glycol ethers of steareth alcohol, wherein the numeric designation indicates the number of ethylene oxide moieties present; the laureth series of compounds such as laureth-5 through laureth-40, which are ethylene glycol ethers of lauryl alcohol, wherein the numeric designation indicates the number of ethylene oxide moieties present; ceteareth 5 through ceteareth-50, which are the ethylene glycol ethers of ceteareth alcohol, i.e. a mixture of fatty alcohols containing predominantly cetyl and stearyl alcohol, wherein the numeric designation indicates the number of ethylene oxide moieties present; $C_6$–$C_{30}$ alkyl ethers of the ceteth, steareth, and ceteareth compounds just described; the pareth series of compounds such as pareth-5 through pareth-40, which are ethylene glycol ethers of synthetic fatty alcohols containing both even- and odd-carbon chain length fractions, wherein the numeric designation indicates the number of ethylene oxide moieties present; and mixtures thereof. Especially preferred ethoxylated fatty alcohols are those selected from the group consisting of ceteth-10, ceteth-20, steareth-10, steareth-20, steareth-21, steareth-100, laureth- 12, laureth-23, ceteareth-20, C12–13 pareth-7, C12–15 pareth-9, C14–15 pareth-13, and mixtures thereof. These and other nonlimiting examples of the ethoxylated fatty alcohols, are found in *International Cosmetic Ingredient Dictionary*, Fifth Edition, 1993, and *CTFA Cosmetic Ingredient Handbook*, Second Edition, 1992, both of which are incorporated by reference herein in their entirety.

Commercially available ethoxylated fatty alcohols for use in the shampoo composition include compounds marketed under the tradenames Brij 35, Lipocol L-12, Brij 56, Brij 58, Brij 68, Brij 76, Brij 78, Brij 721, and Brij 700, all of which are commercially available from ICI Surfactant and Lipo Chemicals, and Neodol 23-6.5, Neodol 25-9, and Neodol 35-13 which are commercially available from Shell Chemical.

Conditioning Agent

The shampoo compositions of the present invention comprise from about 0.01% to about 20%, preferably from about 0.05% to about 10%, more preferably from about 0.1% to about 5%, and even more preferably from about 0.5% to about 3% of dispersed particles of a nonvolatile hair or skin conditioning agent. Suitable hair or skin conditioning agents include nonvolatile silicone conditioning agents, nonvolatile hydrocarbon conditioning agents, and mixtures thereof.

Average particle size of the dispersed conditioning agent particles range must range from about 5 um to about 2000 um. For hair care applications, the average particles size is preferably from about 5 um to about 500 um, more preferably from about 10 um to about 200 um, even more preferably form about 15 um to about 100 um, and most preferably from 20 um to about 75 um. For skin care applications, the average particle size may preferably ranges from about 500 um to about 2000 um, more preferably from about 600 um to about 1500 um, even more preferably from about 800 um to about 1200 um.

It has been found that the average particle size range for the nonvolatile conditioning agent particles must range from about 5 um to about 200 um in order to provide improved deposition as described herein. The improved deposition is not realized if the average particle size is less than about 5 um, or if the select ethoxylated alcohols are not used in the composition.

As used herein, average particle size of the conditioning agent particles may be measured within the shampoo compositions by light scattering methods well known in the art for determining average particle size for emulsified liquids. One such method involves the use of a Horiba LA-910 particle size analyzer.

Silicone Conditioning Agents

Preferred conditioning agents useful herein include nonvolatile, dispersed silicone conditioning agents. By nonvolatile is meant that the silicone conditioning agent exhibits very low or no significant vapor pressure at ambient conditions, e.g., 1 atmosphere at 25° C. The nonvolatile silicone conditioning agent preferably has a boiling point at ambient pressure of above about 250° C., preferably of above about 260° C., and more preferably of above about 275° C. By dispersed is meant that the conditioning agent forms a separate, discontinuous phase from the aqueous carrier such as in the form of an emulsion or a suspension of droplets.

The nonvolatile silicone hair conditioning agents for use herein preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970, which is incorporated by reference herein in its entirety. Suitable silicone fluids include polyalkyl siloxanes, polyaryl siloxanes, polyalkylaryl siloxanes, polyether siloxane copolymers, and mixtures thereof. Other nonvolatile silicones having hair conditioning properties can also be used.

The silicones herein also include polyalkyl or polyaryl siloxanes with the following structure:

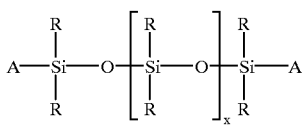

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicones are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The silicones that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicones include amino substituted materials. Suitable alkylamino substituted silicones include those represented by the following structure (II)

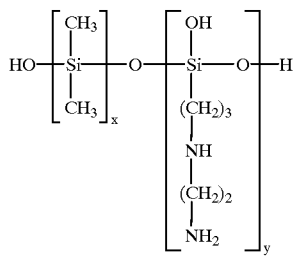

wherein x and y are integers which depend on the molecular weight, the average molecular weight being approximately between 5,000 and 10,000. This polymer is also known as "amodimethicone".

Suitable cationic silicone fluids include those represented by the formula (III) $(R_1)_a G_{3-a}—Si—(—OSiG_2)_n—(—OSiG_b(R_1)_{2-b})_m—O—SiG_{3-a}(R_1)_a$ in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups

—N($R_2$)$CH_2$—$CH_2$—N($R_2$)$_2$

—N($R_2$)$_2$

—N($R_2$)$_3$A$^-$

—N($R_2$)$CH_2$—$CH_2$—NR$_2$H$_2$A$^-$ in which $R_2$ is chosen from the group consisting of hydrogen, phenyl, benzyl, a saturated hydrocarbon radical, preferably an alkyl radical containing from 1 to 20 carbon atoms, and A$^-$ denotes a halide ion.

An especially preferred cationic silicone corresponding to formula (III) is the polymer known as "trimethylsilylamodimethicone", of formula (IV):

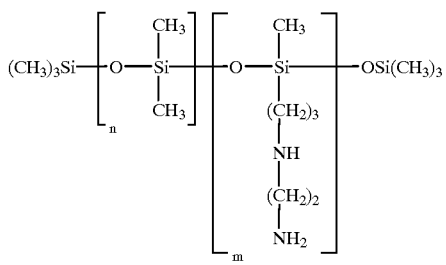

In this formula n and m are selected depending on the exact molecular weight of the compound desired.

Other silicone cationic polymers which can be used in the shampoo compositions are represented by the formula (V):

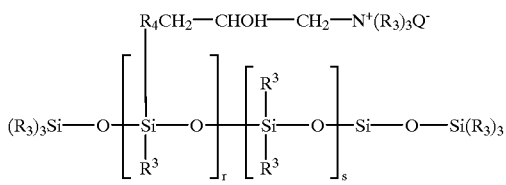

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

References disclosing suitable silicones include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicones.

Another silicone hair conditioning material that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicones. This overlap is not intended as a limitation on any of these materials. Silicone gums are described by Petrarch, Id., and others including U.S. Pat. No. 4,152,416, to Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Also useful are silicone resins, which are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being limited by theory, it is believed that the silicone resins can enhance deposition of other silicones on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

Background material on silicones, including sections discussing silicone fluids, gums, and resins, as well as the manufacture of silicones, can be found in Encyclopedia of Polymer Science and Engineering, Volume 15, Second Edition, pp 204–308, John Wiley & Sons, Inc., 1989, which is incorporated herein by reference in its entirety.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, r and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1 0 and the average molecular weight of the resin is from about 1000 to about 10,000.

Hydrocarbon Conditioning Agents

Other suitable hair conditioning agents for use in the shampoo composition include nonvolatile organic conditioning agents. Suitable nonvolatile organic conditioning agents for use in the composition are those conditioning agents that are known or otherwise effective for use as hair or skin conditioning agent.

The nonvolatile hydrocarbons for use in the shampoo composition may be saturated or unsaturated, and may be straight, cyclic or branched chain. By nonvolatile is meant that the hydrocarbon conditioning agent exhibits very low or no significant vapor pressure at ambient conditions, e.g., 1 atmosphere at 25° C. The nonvolatile hydrocarbon agent preferably has a boiling point at ambient pressure of above about 250° C., preferably above about 260° C., and more preferably of above about 275° C. The nonvolatile hydrocarbons preferably have from about 12 to about 40 carbon atoms, more preferably from about 12 to about 30 carbon atoms, and most preferably from about 12 to about 22 carbon atoms. Also encompassed herein are polymeric hydrocarbons of alkenyl monomers, such as polymers of $C_2$–$C_{12}$ alkenyl monomers, including 1-alkenyl monomers such as polyalphaolefin monomers. These polymers can be straight or branched chain polymers. The straight chain polymers will typically be relatively short in length, having a total number of carbon atoms as described above in this paragraph. The branched chain polymers can have substantially higher chain lengths. Also useful herein are the various grades of mineral oils. Mineral oils are liquid mixtures of hydrocarbons that are obtained from petroleum.

Specific examples of suitable nonvolatile hydrocarbons include, but are not limited to, paraffin oil, mineral oil, dodecane, isododecane, hexadecane, isohexadecane, eicosene, isoeicosene, tridecane, triglyceride oils, tetradecane, polybutene, polyisobutene, and mixtures thereof. Isododecane, isohexadeance, and isoeicosene are commercially available as Permethyl 99A, Permethyl 101A, and Permethyl 1082, from Presperse, South Plainfield, N.J. A copolymer of isobutene and normal butene is commercially available as Indopol H-100 from Amoco Chemicals. Preferred among these hydrocarbons are mineral oil, isododecane, isohexadecane, polybutene, polyisobutene, and mixtures thereof.

Water

The shampoo compositions of the present invention are aqueous systems which comprise an aqueous carrier, typically water. The exact level of water will vary with the levels of the remaining components present. Generally, the shampoo compositions of the present invention comprise from about 20% to about 94.85%, preferably from about 50% to about 92%, and more preferably from about 60% to about 90% water.

Optional Components

In addition to the essential components described hereinbefore, the shampoo compositions may further comprise one or more optional components that are known or otherwise suitable for use on human hair or skin. Nonlimiting examples of such optional components are disclosed in *International Cosmetic Ingredient Dictionary*, Fifth Edition, 1993, and *CTFA Cosmetic Ingredient Handbook*, Second Edition, 1992, both of which are incorporated by reference herein in their entirety. Some nonlimiting examples of such optional components are disclosed below.

Polyalkylene Glycols

The shampoo composition may further comprise a polyalkylene glycol to improve lather performance. Concentration of the polyalkylene glycol in the shampoo composition may range from about 0.01% to about 5%, preferably from about 0.05% to about 3%, and more preferably from about 0.1% to about 2%, by weight of the composition.

The optional polyalkylene glycols are characterized by the general formula:

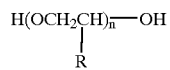

wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

In the above structure, n has an average value of from about 1500 to about 25,000, preferably from about 2500 to about 20,000, and more preferably from about 3500 to about 15,000.

Polyethylene glycol polymers useful herein are PEG-2M wherein R equals H and n has an average value of about 2,000 (PEG-2M is also known as Polyox WSR® N-10, which is available from Union Carbide and as PEG-2,000); PEG-5M wherein R equals H and n has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein R equals H and n has an average value of about 7,000 (PEG-7M is also known as Polyox WSR® N-750 available from Union Carbide); PEG-9M wherein R equals H and n has an average value of about 9,000 (PEG 9-M is also known as Polyox WSR® N-3333 available from Union Carbide); and PEG-14 M wherein R equals H and n has an average value of about 14,000 (PEG-14M is also known as Polyox WSR® N-3000 available from Union Carbide).

Other useful polymers include the polypropylene glycols and mixed polyethylene/polypropylene glycols.

Suspending Agents

The shampoo compositions of the present invention may further comprise a suspending agent at concentrations effective for suspending the preferred silicone conditioning agent, or other water-insoluble material, in dispersed form in the shampoo compositions. Such concentrations range from about 0.1% to about 10%, preferably from about 0.3% to about 5.0%, by weight of the shampoo compositions.

Optional suspending agents include crystalline suspending agents which can be categorized as acyl derivatives, long chain amine oxides, and mixtures thereof, concentrations of which range from about 0.1% to about 5.0%, preferably from about 0.5% to about 3.0%, by weight of the shampoo compositions. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Other Optional Materials

Other optional materials suitable for use in the shampoo compositions of the present invention include, but are not limited to, preservatives such as benzyl alcohol, benzoic acid, methyl paraben, propyl paraben, imidazolidinyl urea, iodopropynyl butyl carbamate, methylisothiazolinone, methylchloroisothiazolinone; salts and electrolytes such as sodium chloride, potassium chloride, and sodium sulfate; ammonium xylene sulfonate; propylene glycol; polyvinyl alcohol; ethyl alcohol; pH adjusting agents such as citric acid, succinic acid, phosphoric acid, sodium hydroxide, and sodium carbonate; fragrances and colorings to modify the aesthetic appeal of the composition; hydrogen peroxide; sunscreening agents; hair coloring agents; humectants such as glycerol and other polyhydric alcohols; moisturizers; humectants; anti-oxidants; and chelating agents such as EDTA; anti-inflammatory agents; steroids; topical anesthetics; and scalp sensates such as menthol. Cationic conditioning polymers may also be used in the shampoo compositions.

Synthetic esters may also be used in the shampoo composition to provide improved wet hair feel when used in combination with the essential components of the shampoo composition herein, and in particular when used in combination with the organic conditioning oil described hereinbefore. The concentration of the synthetic esters in the shampoo composition may range from about 0.01% to about 1.0%, preferably from about 0.05% to about 0.5%, more preferably from about 0.08% to about 0.3%, by weight of the composition.

Antidandruff agents may also be used in the shampoo compositions. These agents include particulate antidandruff agents such as pyridinethione salts, selenium compounds such as selenium disulfide, and soluble antidandruff agents. The concentration of antidandruff agents in the shampoo composition may range from about 0.1% to about 4% and preferably about 0.2% to about 2%, by weight of the composition.

Pediculicides can also be used in the shampoo compositions for control of lice infestations. Suitable pediculicides are well known in the art and include, for example, pyrethrins such as those described in U.S. Pat. No. 4,668,666, which description is incorporated herein by reference in its entirety.

METHOD OF USE

The shampoo compositions of the present invention may be used in a conventional manner for cleansing and conditioning human hair or skin. An effective amount of the composition, typically from about 1 gram to about 50 grams, preferably from about 1 gram to about 20 grams, is applied to the hair or skin. Preferably the hair or skin has been wetted with water before application of the composition. Application of the shampoo typically includes working the composition through the hair, generally with the hands and fingers, to generate a lather. The composition is then rinsed from the hair or skin with water.

The method for cleansing and conditioning the hair comprises the steps of:
(a) wetting the hair with water,
(b) applying an effective amount of the composition to the hair,
(c) shampooing the hair with the composition, i.e. working the composition in contact with the hair and into a lather, and
(d) rinsing the composition from the hair using water.

The method for cleansing and conditioning the skin comprises the steps of:
(a) applying an effective amount of the composition to the skin, and
(b) rinsing the composition from the skin using water.

These steps can be repeated as many times as desired to achieve the cleansing and conditioning benefit sought.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are hereinafter identified by chemical, trade, or CTFA name.

Preparation

The shampoo compositions of the present invention can be prepared by using conventional mixing and formulating techniques. The shampoo compositions illustrated hereinafter in Examples I–XX are prepared in the following manner.

If the conditioning agent in the shampoo composition is a silicone conditioning agent, a silicone premix may be prepared by adding 70% dimethicone, 29% ammonium laureth-3 sulfate (solution basis, 26% active) and 1% sodium chloride, all by weight of the silicone premix, to a high shear mixing vessel and mixing for about 30 minutes or until the desired silicone particle size is achieved (preferably an average particle size of from about 20 microns to about 75 microns). A conventional silicone emulsion may also be used.

For each of the shampoo compositions illustrated hereinafter in Examples I–XX, about one-third to all of the total alkyl sulfate surfactant is added to a jacketed mix tank and heated to about 74° C. with slow agitation to form a surfactant solution. Polyquat 10 polymers, polyethylene glycol, insoluble liquid ester, oil, cocamide monoethanolamide and cocamide diethanolamide and other minor ingredients, as applicable, are added to the tank and allowed to disperse. Ethylene glycol distearate (EGDS) is then added to the mixing vessel, and melted. After the EGDS is well dispersed (usually after about 5 to 20 minutes) optional preservative are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the ammonium laureth sulfate, lauryl sulfate or cocamidopropylbetaine are then added to a separate jacketed mix tank and heated to about 74° C. with slow agitation to form a surfactant solution. The ethoxylated fatty alcohol is then added and allowed to dissolve. The solution is then allowed to cool to below 30° C. This solution, together with the rest of the ingredients including the silicone premix, if applicable, are added to the finishing tank with ample agitation to insure a homogeneous mixture. A sufficient amount of the silicone premix is added to provide the desired level of dimethicone in the final product. Once all ingredients have been added, ammonium xylene sulfonate or additional sodium chloride can be added to the mixture to thin or thicken respectively to achieve a desired product viscosity. Preferred viscosities range from about 3500 to about 9000 centistokes at 25° C. (as measured by a Wells-Brookfield cone and plate viscometer at 2/s at 3 minutes).

Average particle size of the conditioning agent particles in each of the exemplified compositions is from about 30 um to about 40 um.

| Ingredient | Example Number | | | | |
|---|---|---|---|---|---|
| | I | II | III | IV | V |
| Ammonium Laureth-3 Sulfate | 10 | 6 | 10 | 12 | 10 |
| Ammonium Lauryl Sulfate | 6 | 10 | 6 | 4 | 6 |
| Dimethicone[1] | 1.5 | 2.0 | 1.5 | 2.0 | 1.5 |
| Ceteth-10[2] | 3 | 2 | 0 | 0 | 0 |
| Laureth-12[3] | 0 | 0 | 3 | 2 | 0 |
| Poloxyl 7 myristyl ether[4] | 0 | 0 | 0 | 0 | 3 |
| Polyethylene Glycol[5] | 0.2 | 0.2 | 0 | 0 | 0.2 |
| Cocamide MEA | 0.90 | 0.60 | 0.90 | 1.00 | 0.90 |
| Ethylene Glycol Distearate | 1.50 | 1.20 | 1.50 | 1.50 | 1.50 |
| Fragrance | 0.50 | 0.50 | 0.50 | 0.50 | 0.50 |
| DMDM Hydantoin | 0.20 | 0.20 | 0.20 | 0.20 | 0.20 |
| Water and minors | q.s. to 100% | | | | |

-continued

| Ingredient | Example Number | | | | |
|---|---|---|---|---|---|
| | VI | VII | VIII | IX | X |
| Ammonium Laureth-3 Sulfate | 12 | 12 | 10 | 10 | 10 |
| Ammonium Lauryl Sulfate | 4 | 4 | 6 | 6 | 6 |
| Polyquaternium-10[6] | 0.5 | 0.4 | 0.3 | 0.5 | 0.4 |
| Mineral Oil[7] | 0 | 0.4 | 0.5 | 0 | 0 |
| Hydrogenated Polyalpha Olefin[8] | 0.25 | 0 | 0 | 0.4 | 0.3 |
| Trimethylolpropane caprylate caprate[9] | 0.25 | 0 | 0 | 0.1 | 0.2 |
| Dimethicone[1] | 1.8 | 1.5 | 1.5 | 1.5 | 2.0 |
| Ceteth-10[2] | 3 | 3 | 2 | 3 | 0 |
| Laureth-12[3] | 0 | 0 | 1 | 0 | 3 |
| Cocamide MEA | 0.9 | 0.9 | 0 | 0 | 0 |
| Cocamide DEA | 0 | 0 | 0.9 | 0.9 | 0.9 |
| Ethylene Glycol Distearate | 1.50 | 1.50 | 1.40 | 1.40 | 1.30 |
| Fragrance | 0.50 | 0.50 | 0.50 | 0.50 | 0.50 |
| DMDM Hydantoin | 0.20 | 0.20 | 0.20 | 0.20 | 0.20 |
| Water and minors | q.s. to 100% | | | | |

| | XI | XII | XIII | XIV | XV |
|---|---|---|---|---|---|
| Ammonium Laureth-3 Sulfate | 14 | 14 | 12 | 12 | 12 |
| Cocamidopropylbetaine | 2.7 | 2.7 | 4.5 | 4.5 | 4.0 |
| Polyquaternium-10[10] | 0.15 | 0.2 | 0 | 0.15 | 0.2 |
| Dimethicone[1] | 1.5 | 1.25 | 2.0 | 1.5 | 1.5 |
| Ceteth-10[2] | 3 | 0 | 2 | 0 | 3 |
| Laureth-12[3] | 0 | 3 | 0 | 3 | 0 |
| Polyethylene Glycol[11] | 0.25 | 0 | 0.25 | 0.25 | 0.25 |
| Cocamide MEA | 1.0 | 0 | 1.0 | 0 | 1.0 |
| Cocamide DEA | 0 | 0.80 | 0 | 0.70 | 0 |
| Ethylene Glycol Distearate | 1.50 | 1.50 | 1.40 | 1.40 | 1.60 |
| Fragrance | 0.50 | 0.50 | 0.50 | 0.50 | 0.50 |
| DMDM Hydantoin | 0.20 | 0.20 | 0.20 | 0.20 | 0.20 |
| Water and minors | q.s. to 100% | | | | |

| | XVI | XVII | XVIII | XIX | XX |
|---|---|---|---|---|---|
| Ammonium Laureth-3 Sulfate | 12 | 12 | 11 | 11 | 11 |
| Ammonium Lauryl Sulfate | 4 | 4 | 0 | 0 | 0 |
| Cocamidopropylbetaine | 0 | 0 | 4.5 | 4.5 | 5.0 |
| Polyquaternium-10[12] | 0.5 | 0 | 0 | 0.5 | 0.5 |
| Mineral Oil[7] | 0.5 | 0 | 0 | 0 | 0 |
| C8/C10 diester of adipic acid[13] | 0.3 | 0.3 | 0.2 | 0.2 | 0.1 |
| Dimethicone[1] | 1.5 | 1.5 | 2.0 | 1.75 | 1.75 |
| Ceteth-10[2] | 2 | 2 | 2 | 2 | 1 |
| Laureth-12[3] | 1 | 1 | 1 | 1 | 2 |
| Cocamide MEA | 0.5 | 05 | 0.6 | 0.6 | 0.6 |
| Ethylene Glycol Distearate | 1.50 | 1.50 | 1.40 | 1.40 | 1.40 |
| Fragrance | 0.50 | 0.50 | 0.50 | 0.50 | 0.50 |
| DMDM Hydantoin | 0.20 | 0.20 | 0.20 | 0.20 | 0.20 |
| Water and minors | q.s. to 100% | | | | |

[1]Dimethicone is a 40(gum)/60(fluid) weight ratio blend of SE-76 dimethicone gum available from General Electric Silicones Division and a dimethicone fluid having a viscosity of 350 centistokes.
[2]Brij 56 from ICI Surfactant
[3]Lipocol L-12 from Lipo Chemicals
[4]Neodol 45-7 from Shell Chemicals
[5]Polyox N-3000 from Union Carbide
[6]LR 400 available from Amerchol
[7]Benol light white Mineral Oil from Witco
[8]SHF 62 available from Mobil Chemical
[9]P43 available from Mobile Chemical
[10]JR 30 M available from Amerchol
[11]Polyox N-750 from Union Carbide
[12]JR 400 available from Amerchol
[13]MCP 121 available from Mobil Chemical The shampoo compositions illustrated in Examples I–XX, all of which are embodiments of the present invention, provide excellent cleansing and conditioning of hair or skin, and further enhance cleaning and conditioning impression by providing select ethoxylated fatty alcohols which provide improved deposition of the conditioning agents onto hair or skin.

COMPARATIVE EXAMPLE

The shampoo compositions illustrated in the following examples are comparative examples which show how the improved silicone deposition of a shampoo composition of the present invention compares to other shampoo compositions. More specifically, the examples show how the silicone deposition of shampoo compositions containing either ceteth-10 or steareth-10 compares to similar compositions which contain neither ceteth-10 nor steareth-10. Each formulation is prepared in a manner similarly described for Examples I–XX hereinabove.

Methodologies for measuring or otherwise identifying improved silicone deposition on hair or other surfaces are well known in the art. Such methods can be used to measure or identify the improved nonvolatile conditioning agent deposition described herein. The term "ppm" as used herein refers to parts per million.

| Ingredient | Formulation I | Formulation II |
|---|---|---|
| Comparative Examples of Silicone Deposition with Ceteth-10 | | |
| Ammonium Laureth-3 Sulfate | 10 | 10 |
| Ammonium Lauryl Sulfate | 6 | 6 |
| Dimethicone | 1.5 | 1.5 |
| Ceteth-10 | 0 | 3 |
| Cocamide MEA | 0.90 | 0.90 |
| Ethylene Glycol Distearate | 1.50 | 1.50 |
| Monosodium Phosphate | 0.10 | 0.10 |
| Desodium Phosphate | 0.20 | 0.20 |
| Fragrance | 0.50 | 0.50 |
| DMDM Hydantoin | 0.20 | 0.20 |
| Color Solution | 0.64 | 0.64 |
| Perfume | 0.60 | 0.60 |
| Sodium Benzoate | 0.25 | 0.25 |
| Sodium Chloride | 1.0 | 1.0 |
| Water and minors | q.s. to 100% | q.s. to 100% |
| Silicone Deposited: | 541 ppm (control) | 1020 ppm (89% increase) |
| Comparative Examples of Silicone Deposition with Steareth-10 | | |
| Ammonium Laureth-3 Sulfate | 10 | 10 |
| Ammonium Lauryl Sulfate | 6 | 6 |
| Dimethicone | 1.5 | 1.5 |
| Steareth | 0 | 3 |
| Cocamide MEA | 0.90 | 0.90 |
| Ethylene Glycol Distearate | 1.50 | 1.50 |
| Monosodium Phosphate | 0.10 | 0.10 |
| Desodium Phosphate | 0.20 | 0.20 |
| Fragrance | 0.50 | 0.50 |
| DMDM Hydantoin | 0.20 | 0.20 |
| Color Solution | 0.64 | 0.64 |
| Perfume | 0.60 | 0.60 |
| Sodium Benzoate | 0.25 | 0.25 |
| Sodium Chloride | 1.0 | 1.0 |
| Water and minors | q.s. to 100% | q.s. to 100% |
| Silicone Deposited: | 975 ppm (control) | 2259 ppm (132% increase) |

From the comparative examples above, it is shown that the shampoo compositions which contain ceteth-10 or steareth-10 deposit more silicone onto a surface such as hair than do the other compositions which contain neither of these ethoxylated alcohols.

What is claimed is:

1. A hair conditioning shampoo composition comprising:
   (a) from about 5% to about 50% by weight of a detersive surfactant selected from the group consisting of anionic surfactant, nonionic surfactant, amphoteric surfactant, zwitterionic surfactant, and mixtures thereof;
   (b) from about 0.1% to about 10% by weight of an ethoxylated fatty alcohol having a fatty alcohol moiety containing from about 6 to about 30 carbon atoms and an ethoxylate chain having from 7 to about 150 moles of ethoxylation;
   (c) from about 0.01% to about 20% by weight of dispersed particles of a nonvolatile hair conditioning agent having an average particle size of from about 5 um to about 500 um;
   (d) from about 0.1% to about 10% of a suspending agent selected from the group consisting of crystalline suspending agents, xanthan gum, carboxyvinyl polymers, crosslinked maleic anhydride-methyl vinyl copolymer, guar gum, polyvinyl pyrrolidone, hydroxypropyl guar gum, starch and starch derivatives; and
   (e) from about 10% to about 95.79% by weight water.

2. The composition of claim 1 wherein the hair conditioning agent is selected from the group consisting of nonvolatile silicone conditioning agents, hydrocarbon conditioning agents, and mixtures thereof.

3. The composition of claim 1 wherein the hair conditioning agent is a silicone conditioning agent, and the detersive surfactant is an anionic detersive surfactant.

4. The composition of claim 3 wherein the silicone conditioning agent is dimethicone.

5. The composition of claim 3 wherein said composition comprises from about 0.5% to about 4% by weight of the ethoxylated fatty alcohol.

6. The composition of claim 3 wherein the average particle size of the silicone conditioning agent is from about 20 um to about 75 um.

7. A hair composition for cleansing and conditioning the skin, comprising:
   (a) from about 5% to about 50% by weight of a detersive surfactant selected from the group consisting of anionic surfactant, amphoteric surfactant, zwitterionic surfactant, and mixtures thereof;
   (b) from about 0.1% to about 10% by weight of an ethoxylated fatty alcohol having a fatty alcohol moiety containing from about 6 to about 30 carbon atoms and an ethoxylate chain having from 7 to about 150 moles of ethoxylation;
   (c) from about 0.01% to about 20% by weight of dispersed particles of a nonvolatile hair conditioning agent having an average particle size of from about 600 um to about 2000 um;
   (d) from about 0.1% to about 10% of a suspending agent selected from the group consisting of crystalline suspending agents, xanthan gum, carboxyvinyl polymers, crosslinked maleic anhydride-methyl vinyl copolymer, guar gum, polyvinyl pyrrolidone, hydroxypropyl guar gum, starch and starch derivatives; and
   (e) from about 10% to about 94.79% by weight water.

8. The composition of claim 7 wherein the skin conditioning agent is selected from the group consisting of nonvolatile silicone conditioning agents, hydrocarbon conditioning agents, and mixtures thereof.

9. The composition of claim 8 wherein the skin conditioning agent is a silicone conditioning agent, and the detersive surfactant is an anionic detersive surfactant.

10. The composition of claim 9 wherein the silicone conditioning agent is dimethicone.

11. The composition of claim 8 wherein said composition comprises from about 0.5% to about 4% by weight of the ethoxylated fatty alcohol.

12. The composition of claim 11 wherein the ethoxylated fatty alcohol has a fatty alcohol moiety having from about 10 to about 19 carbon atoms, and an ethoxylate chain having from about 7 to about 21 moles of ethoxylation.

13. The composition of claim 12 wherein the ethoxylated fatty alcohol is selected from the group consisting of ceteth-10, ceteth-20, steareth-10, steareth-20, steareth-21, laureth-12, ceteareth-20, C12–13 pareth-7, C12–15 pareth-9, C14–15 pareth-13, and mixtures thereof.

14. The composition of claim 13 wherein the ethoxylated fatty alcohol is selected from the group consisting of ceteth-10, laureth-12, steareth-10, and mixtures thereof.

15. The composition of claim 9 wherein the average particle size of the silicone conditioning agent is from about 800 um to about 1200 um.

16. A method for cleansing and conditioning the hair, which method comprises the steps of:
  (a) wetting the hair with water,
  (b) applying from about 1 gram to about 50 grams of the composition of claim 1 to the hair,
  (c) shampooing the hair with the composition, and
  (d) rinsing the composition from the hair using water.

17. A method for cleansing and conditioning the skin, which method comprises the steps of:
  (a) applying from about 1 gram to about 50 grams of the composition of claim 8 to the skin, and
  (b) rinsing the composition from the skin using water.

18. The composition of claim 1 wherein the suspending agent is a crystalline suspending agent.

19. The composition of claim 18 wherein the suspending agent is ethylene glycol distearate.

20. The composition of claim 19 wherein the ethoxylated fatty alcohol is selected from the group consisting of ceteth-10, ceteth-20, steareth-10, steareth-20, steareth-21, laureth-12, laureth-23, ceteareth-20, C12–13 pareth-7, C12–15 pareth-9, C14–15 pareth-13, and mixtures thereof.

21. The composition of claim 20 wherein the ethoxylated fatty alcohol is selected from the group consisting of ceteth-10, laureth-12, steareth-10, and mixtures thereof.

22. The composition of claim 8 wherein the suspending agent is a crystalline suspending agent.

23. The composition of claim 22 wherein the suspending agent is ethylene glycol distearate.

24. The composition of claim 22 wherein the ethoxylated fatty alcohol is selected from the group consisting of ceteth-10, ceteth-20, steareth-10, steareth-20, steareth-21, laureth-12, laureth-23, ceteareth-20, C12–13 pareth-7, C12–15 pareth-9, C14–15 pareth-13, and mixtures thereof.

* * * * *

UNITED STATES PATENT AND TRADEMARK OFFICE
CERTIFICATE OF CORRECTION

PATENT NO.     : 6,200,554 B1
DATED          : March 13, 2001
INVENTOR(S)    : T.Y. Yeoh et al.

It is certified that error appears in the above-identified patent and that said Letters Patent is hereby corrected as shown below:

Column 21,
Line 42, "Steareth" should read -- Steareth-10 --.

Column 22,
Line 14, "95.79%" should read -- 94.79% --.

Signed and Sealed this

Fifth Day of July, 2005

JON W. DUDAS
*Director of the United States Patent and Trademark Office*